United States Patent
Jeong et al.

(10) Patent No.: US 10,226,477 B2
(45) Date of Patent: Mar. 12, 2019

(54) COMPOSITION FOR PREVENTING, IMPROVING OR TREATING POSTMENOPAUSAL OSTEOPOROSIS COMPRISING SCOPOLIN

(71) Applicant: DONG WOO DANG CO., LTD, Yeongcheon-si, Gyeongsangbuk-do (KR)

(72) Inventors: Seon-Yong Jeong, Yongin-si (KR); Si Young Yang, Suwon-si (KR); Eun Kuk Park, Suwon-si (KR); Jeong Hyun Kim, Suwon-si (KR); Mun-Chang Kim, Suwon-si (KR)

(73) Assignee: DONG WOO DANG CO., LTD, Yeongcheon-si, Gyeongsangbuk-do (KR)

( * ) Notice: Subject to any disclaimer, the term of this patent is extended or adjusted under 35 U.S.C. 154(b) by 0 days.

(21) Appl. No.: 15/447,056

(22) Filed: Mar. 1, 2017

(65) Prior Publication Data

US 2017/0252363 A1    Sep. 7, 2017

(30) Foreign Application Priority Data

Mar. 2, 2016 (KR) .......... 10-2016-0025022
Nov. 9, 2016 (KR) .......... 10-2016-0148813

(51) Int. Cl.
*A61K 31/7048* (2006.01)
*A23L 33/10* (2016.01)

(52) U.S. Cl.
CPC .......... *A61K 31/7048* (2013.01); *A23L 33/10* (2016.08); *A23V 2002/00* (2013.01)

(58) Field of Classification Search
None
See application file for complete search history.

(56) References Cited

PUBLICATIONS

Lee ,Journal of Natural Products, 2013, 76, 615-620.*
KR20070093226A, published Mar. 13, 2006, machine translation.*
McClung, Arthritis Research & Therapy 2007, 9(Suppl 1):S3.*
Ding, Biol. Pharm. Bull. 33(8) 1448-1453 (2010).*

* cited by examiner

*Primary Examiner* — Layla D Berry
(74) *Attorney, Agent, or Firm* — Revolution IP, PLLC

(57) ABSTRACT

Provided is a pharmaceutical composition for preventing, improving, or treating postmenopausal osteoporosis in women, the composition including, as an active ingredient, scopolin, a derivative thereof, or a pharmaceutically acceptable salt thereof, wherein scopolin has good efficacy in stimulating osteoblast differentiation, and is also effective in inhibiting a reduction in bone density after menopause, low density in a bone microstructure, a reduction in a bone formation marker in the blood, and an increase in a bone resorption marker. Therefore, scopolin and the composition including the same as an active ingredient are expected to be useful as pharmaceutical preparations for the prevention, improvement, or treatment of postmenopausal osteoporosis in women.

1 Claim, 10 Drawing Sheets

[FIG. 1]
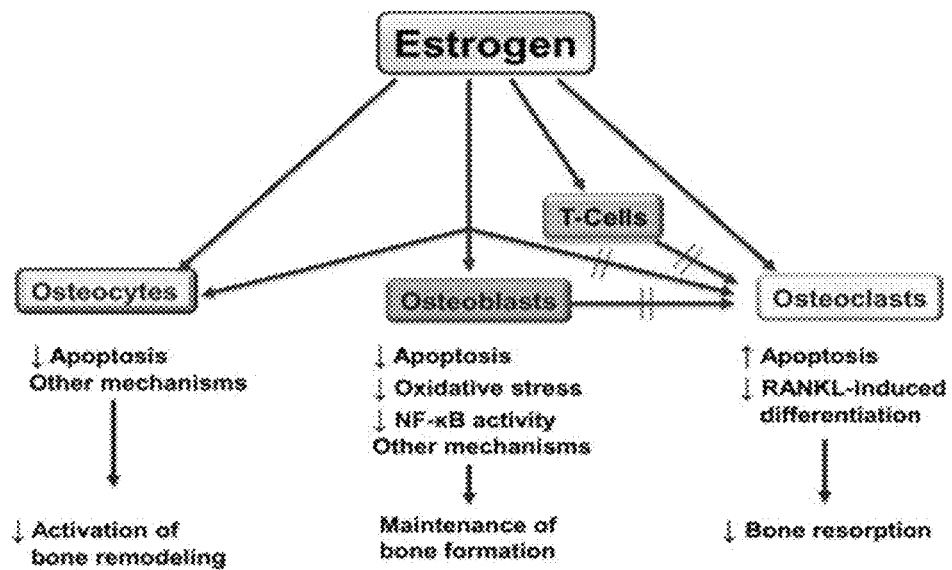
[FIG. 2]
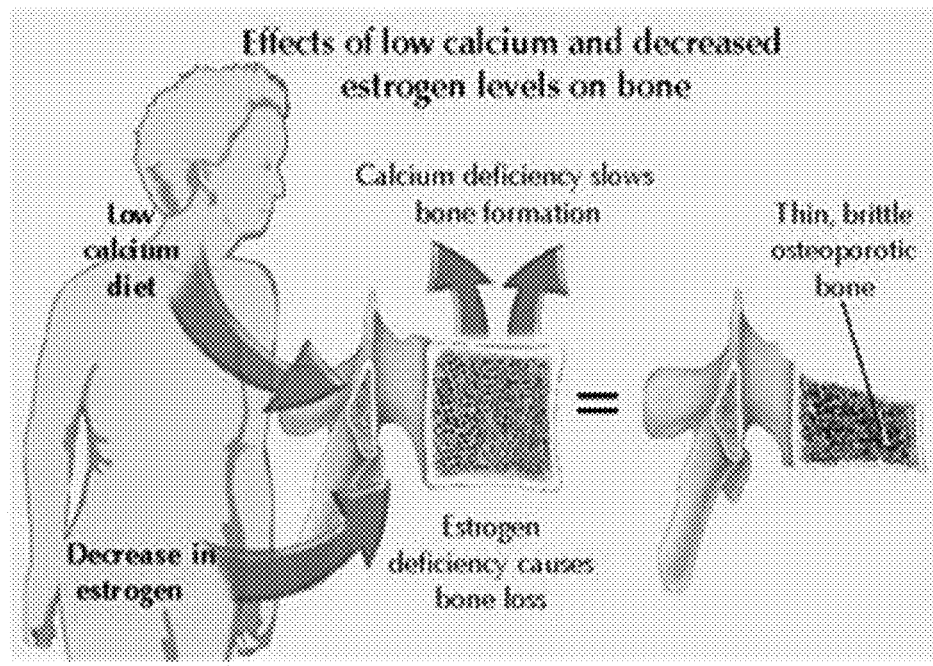

[FIG. 3]
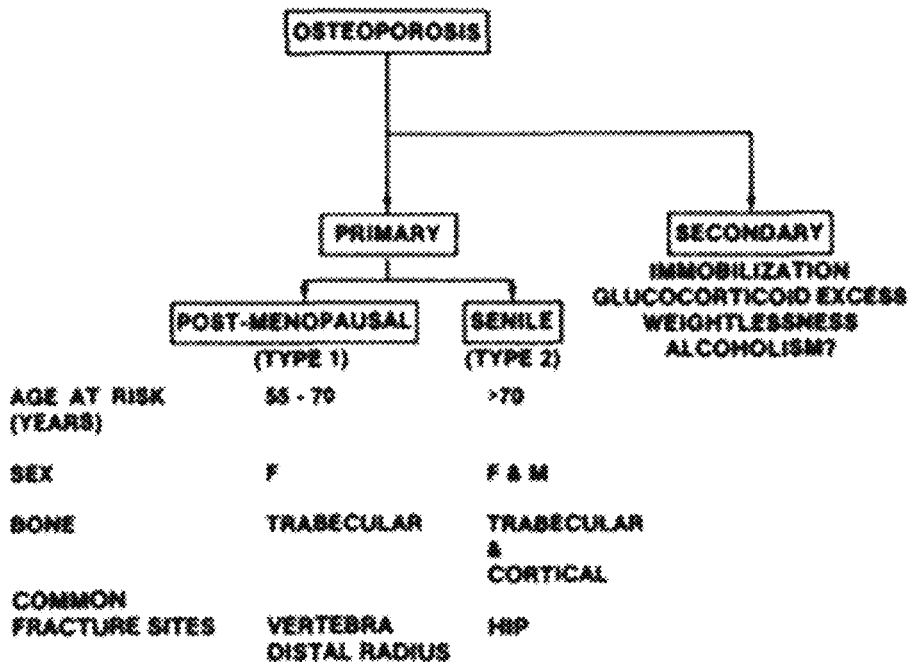
[FIG. 4]
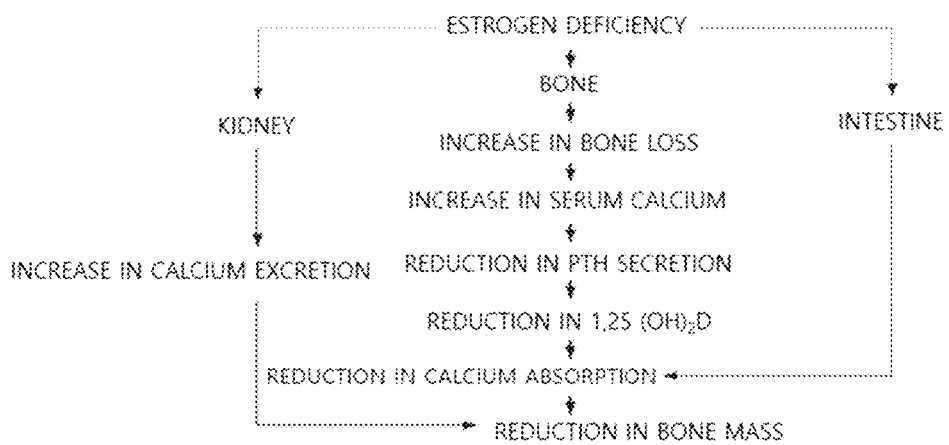

[FIG. 5]
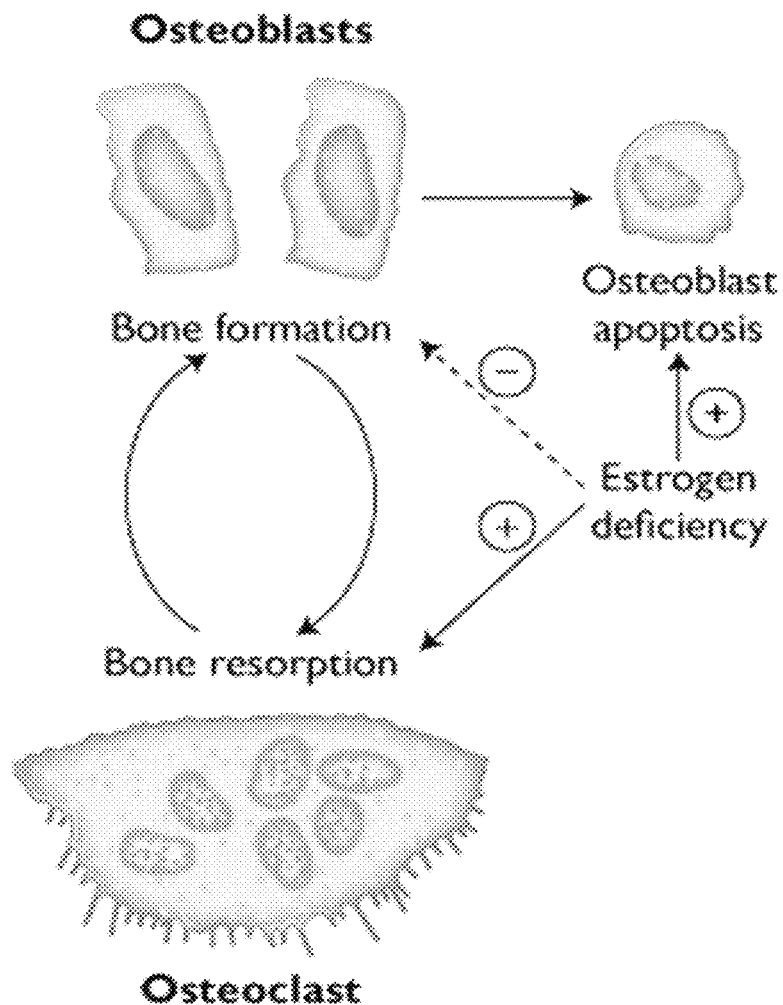
[FIG. 6]
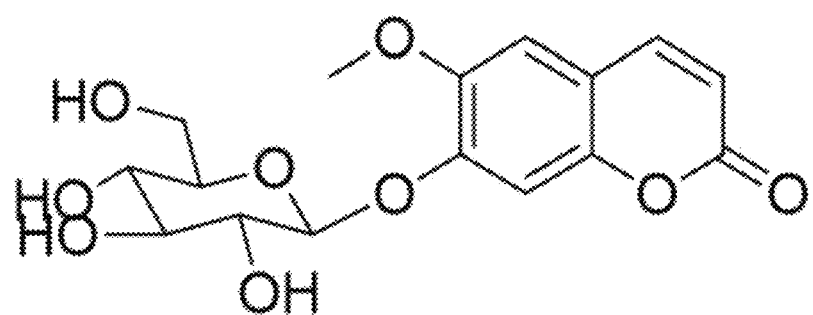

[FIG. 7a]
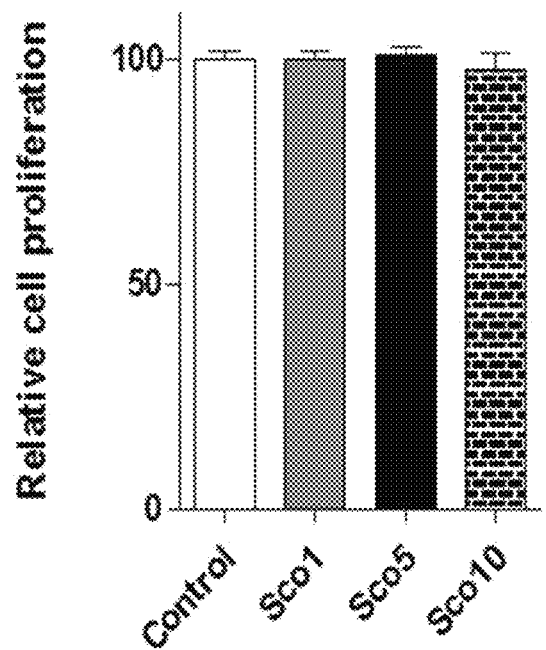
[FIG. 7b]
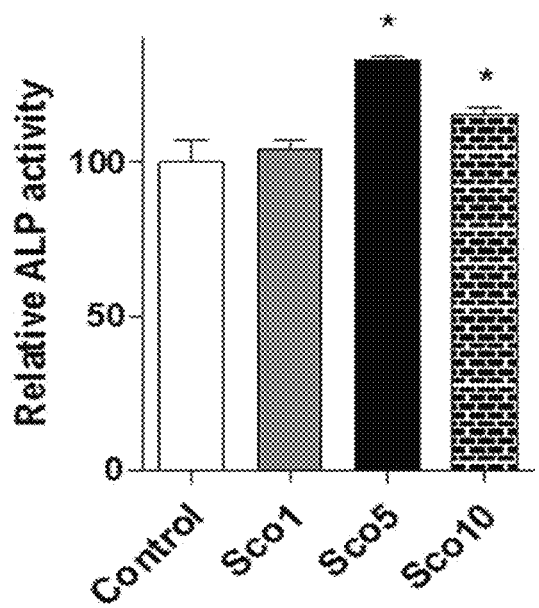

[FIG. 7c]
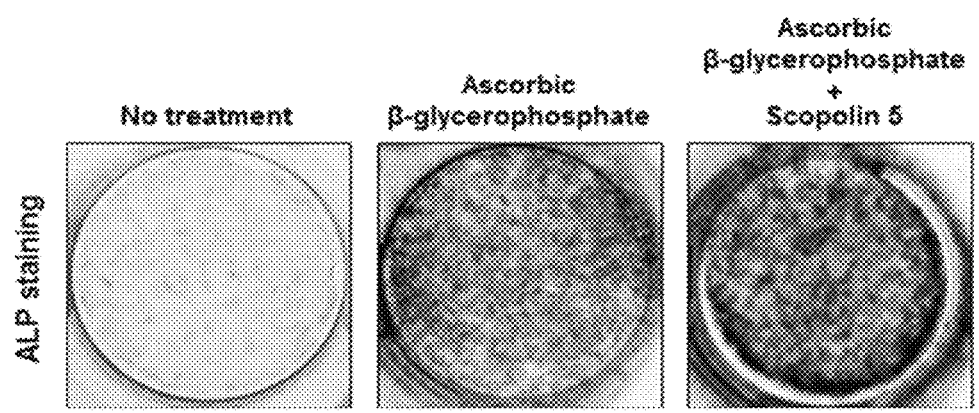
[FIG. 7d]
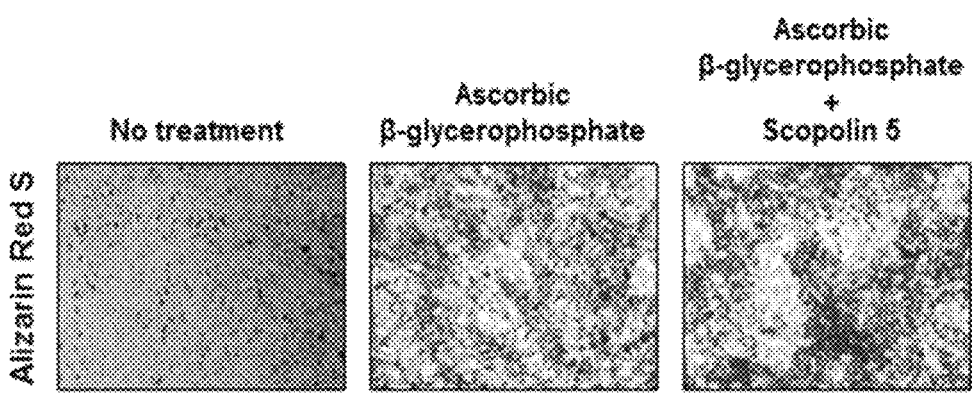

[FIG. 8a]
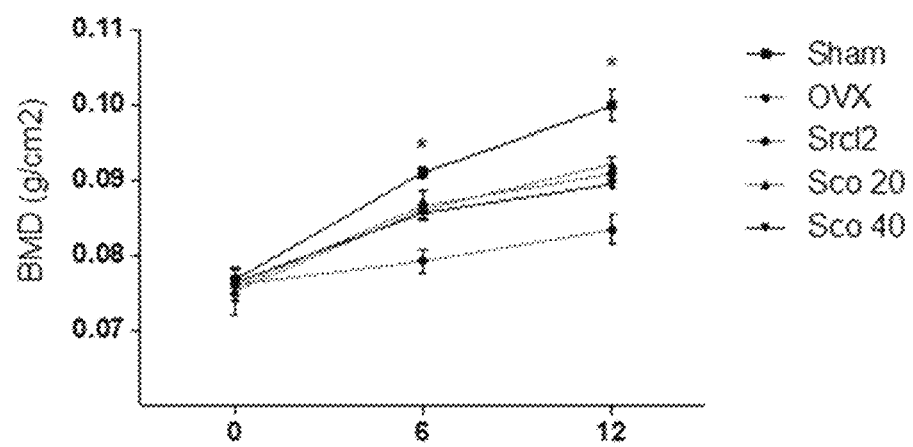
[FIG. 8b]
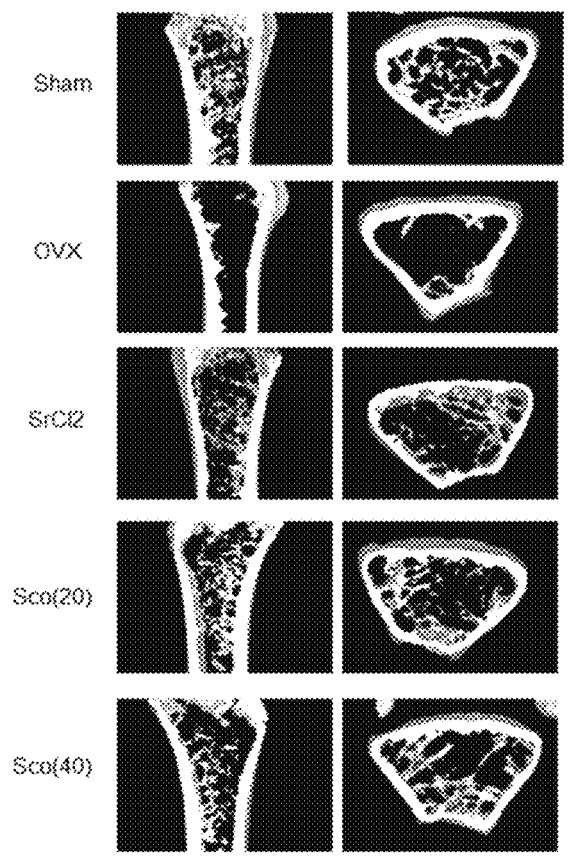

[FIG. 8c]
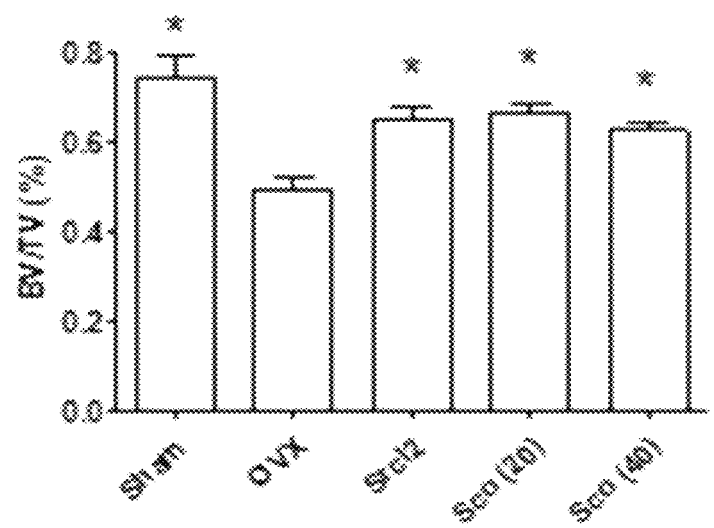
[FIG. 8d]
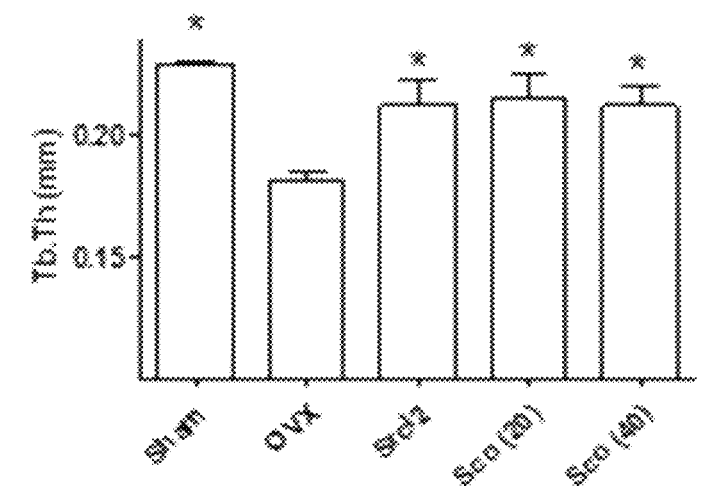

[FIG. 8e]
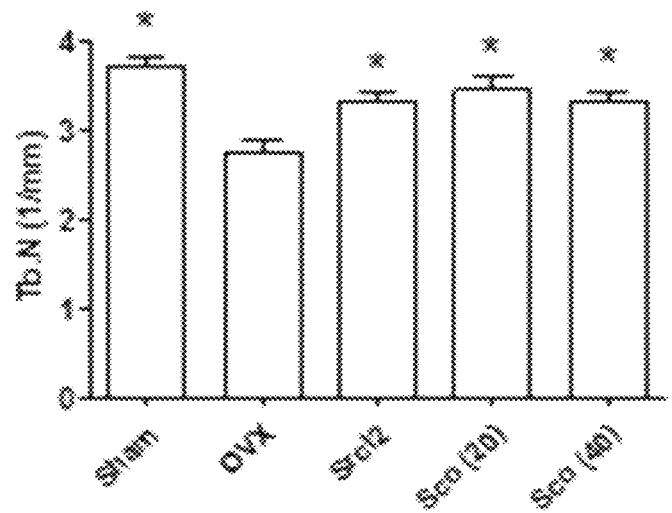
[FIG. 8f]
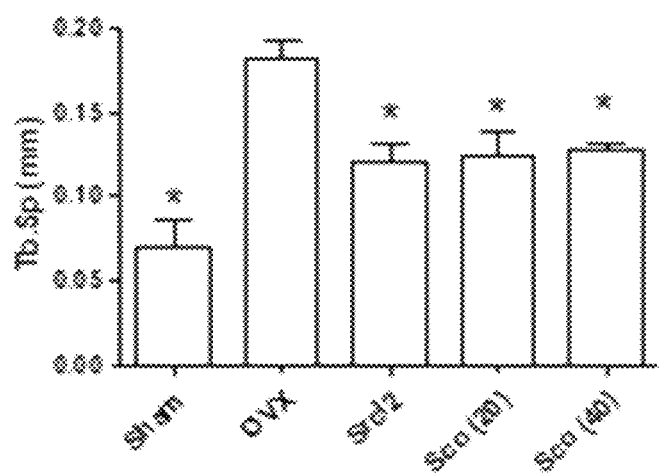

[FIG. 9a]
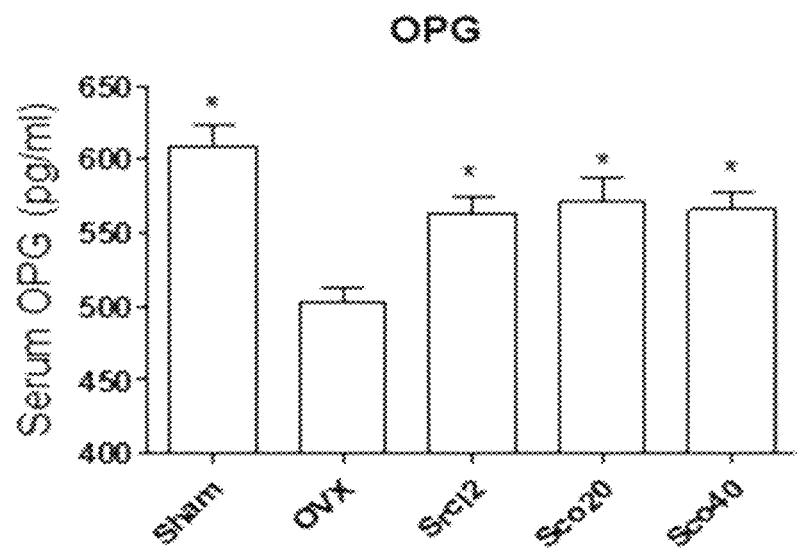
[FIG. 9b]
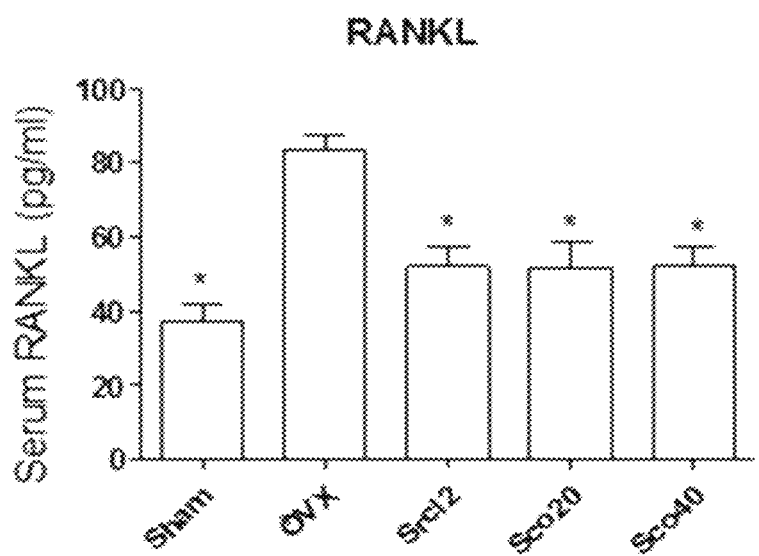

[FIG. 9c]
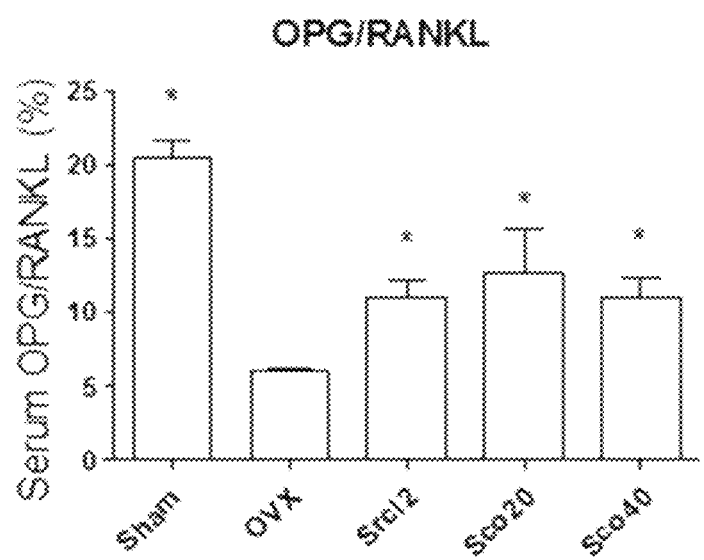

COMPOSITION FOR PREVENTING, IMPROVING OR TREATING POSTMENOPAUSAL OSTEOPOROSIS COMPRISING SCOPOLIN

CROSS REFERENCE TO PRIOR APPLICATIONS

This application claims the benefit of Korean Patent Application No. 10-2016-0025022, filed on Mar. 2, 2016, and Korean Patent Application No. 10-2016-0148813, filed on Nov. 9, 2016, in the Korean Intellectual Property Office, the disclosure of which is incorporated herein in its entirety by reference.

BACKGROUND

1. Field

The present disclosure relates to a composition for preventing, improving, or treating osteoporosis (Type I osteoporosis) in postmenopausal women, the composition including, as an active ingredient, scopolin, a derivative thereof, or a pharmaceutically acceptable salt thereof.

2. Description of the Related Art

Estrogen which is a representative hormone that symbolizes women is an important female hormone that regulates a lifespan of women through menstruation, pregnancy, and menopause. Estrogen is a well-known female hormone that is mainly secreted from follicles and corpus luteum that are in female ovaries and from the placenta, and is a generic term for estrone (E1), estradiol (E2), and estriol (E3). Estrogen affects a wide range of tissues, and is especially needed to maintain flexibility and steady state of the uterus, urinary tract, breast, skin, bones, and blood vessels. In particular, estrogen acts on osteoblast involved in production of bones to maintain bone formation, and also acts on osteoclast involved in removal of bones to inhibit bone resorption, thereby maintaining homeostasis of bones (see FIG. 1). Thus, postmenopausal osteoporosis which is caused by reduced estrogen levels is one of the most serious diseases in postmenopausal women (see FIG. 2).

Osteoporosis is a condition where bone mass per unit volume is abnormally reduced compared to a normal level according to sex, age, and race of a normal person. Due to brittle bones that break easily by minor impacts such as bending the waist or sitting down, osteoporosis is characterized by fractures in the coxa, carpal, vertebrae, or the like. According to pathogenesis of osteoporosis, osteoporosis is divided into primary and secondary forms. Primary osteoporosis includes postmenopausal osteoporosis (Type I osteoporosis) and senile osteoporosis (Type II osteoporosis), and secondary osteoporosis is caused by drugs or the like (see FIG. 3).

Regarding postmenopausal osteoporosis (Type I osteoporosis) in women, when a deficiency of estrogen hormones appears after menopause, postmenopausal osteoporosis occurs as components of bones are absorbed into body tissues and calcium absorption through intestines is reduced (see FIG. 4). In addition, the reduction in estrogen hormones inhibits differentiation and proliferation of osteoblasts, resulting in inhibition of bone formation, and activation of osteoclasts leads to occur bone the resorption more frequently than the bone formation, resulting in an increase of bone loss and a decrease of bone mass (see FIG. 5). The above phenomenon may progress rapidly after menopause depending on a person.

Senile osteoporosis (Type II osteoporosis) is caused by bone loss with increasing age in both men and women. In particular, senile osteoporosis is characterized by a decrease in intestinal calcium absorption due to a reduction in active vitamin D in the body and by a decrease in the number of osteoblasts that newly produce osteocytes. Here, senile osteoporosis progresses relatively slowly herein.

Secondary osteoporosis is caused by various diseases or medications that affect functions related to bone cell production and maintenance of the human body. For example, such various diseases may include hyperthyroidism, hyperparathyroidism, Cushing's syndrome, rheumatoid arthritis, hyperprolactinemia, and the like, and in addition, steroid hormone preparations or thyroid hormone preparations may also cause secondary osteoporosis.

When the climacteric begins, female hormones secreted from the ovaries are reduced due to a decrease or an imbalance in ovarian functions, and accordingly a variety of symptoms may appear. Even after menopause, postmenopausal osteoporosis may occur due to a rapid decrease in bone density and a decrease of bone mass. Since postmenopausal osteoporosis may cause backache or other bone-related diseases, and bone fractures, postmenopausal osteoporosis is considered as a disease that significantly affects the quality of life. In particular, women undergoing premature menopause or having an ovariectomy before age of 50 may be more susceptible to postmenopausal osteoporosis.

As therapeutic agents for postmenopausal osteoporosis in women, incrementally modified composite drugs, such as Bonviva Plus (composition: bisphosphonate-based drugs) and Aclasta (composition: zoledronic acid injection 5 mg), may be used. However, due to side effects of the agents above, the demand for therapeutic agents derived from natural products or health functional foods is increasing. Calcium which is good for bone health, vitamin D, and health functional foods including isoflavones are widely used, but effects thereof are limited. Therefore, there is a need for the development of more effective pharmaceutical preparations or health functional foods for prevention, improvement, and treatment of postmenopausal osteoporosis in women.

SUMMARY

Provided is a pharmaceutical composition for preventing or treating postmenopausal osteoporosis in women, the composition including, as an active ingredient, scopolin, a derivative thereof, or a pharmaceutically acceptable salt thereof. In particular, there is provided a pharmaceutical composition for preventing, improving, and treating osteoporosis and a reduction in postmenopausal bone density caused by a decrease in estrogen hormones in postmenopausal women.

Additional aspects will be set forth in part in the description which follows and, in part, will be apparent from the description, or may be learned by practice of the presented embodiments.

According to an aspect of an embodiment, a pharmaceutical composition for preventing or treating postmenopausal osteoporosis in women includes, as an active ingredient, scopolin, a derivative thereof, or a pharmaceutically acceptable salt thereof.

According to an aspect of another embodiment, a health food composition for preventing or improving postmenopausal osteoporosis includes, as an active ingredient, scopolin, a derivative thereof, or a pharmaceutically acceptable salt thereof According to an aspect of another embodiment, a reagent composition for stimulating osteoblast differentiation, the reagent composition includes, as an active ingredient, scopolin, a derivative thereof, or a pharmaceutically acceptable salt thereof.

According to an aspect of another embodiment, a method of stimulating osteoblast differentiation includes treating osteoblast with scopolin, a derivative thereof, or a pharmaceutically acceptable salt thereof.

BRIEF DESCRIPTION OF THE DRAWINGS

These and/or other aspects will become apparent and more readily appreciated from the following description of the embodiments, taken in conjunction with the accompanying drawings in which:

FIG. 1 is a schematic diagram showing a mechanism of estrogen involved in bone formation and bone resorption;

FIG. 2 is a diagram showing pathogenesis of postmenopausal osteoporosis that develops in case of estrogen deficiency after menopause;

FIG. 3 is a schematic diagram describing types of osteoporosis, wherein postmenopausal osteoporosis is Type I osteoporosis;

FIG. 4 is a diagram showing pathogenesis of postmenopausal osteoporosis (Type I osteoporosis) which is caused by a deficiency of estrogen hormones after menopause in a way that components of bones are absorbed into body tissues and calcium absorption through intestines is reduced;

FIG. 5 is a schematic diagram showing a mechanism of apoptosis and formation inhibition of osteoblasts upon a deficiency of estrogen hormones after menopause and a mechanism of activation of osteoclasts;

FIG. 6 shows a chemical formula of scopolin;

FIGS. 7A to 7D are each a graph showing results of cytotoxic effects of scopolin on MC3T3-E1 cells, which are osteoblasts, treated with scopolin at concentrations of 1 μg/ml, 5 μg/ml, and 10 μg/ml (see FIG. 7A), a graph showing results of measurement of activity of alkaline phosphatase (ALP), which is an osteoblast differentiation marker (see FIG. 7B), a graph showing results of ALP staining (see FIG. 7C), and a graph showing results of analyzing mineralization through Alizarin Red S staining (see FIG. 7D), wherein the results indicate that scopolin is not toxic to osteoblasts and has a significant effect on stimulating osteoblast differentiation;

FIGS. 8A to 8F are each a graph showing changes measured in bone density in a model mouse having menopause (an ovariectomized mouse) after administering scopolin (20 mg/kg/day and 40 mg/kg/day) thereto for 12 weeks (see FIG. 8A), micro-CT images each showing a thigh bone removed from the model mouse 12 weeks after the administration (see FIG. 8B), a graph showing results of numerical analysis on bone volume ratios (%, BV) obtained from the micro-CT images (see FIG. 8C), a graph showing results of numerical analysis on a trabecular thickness (Tb.Th) (see FIG. 8D), a graph showing results of numerical analysis on a trabecular number (Tb.N) (see FIG. 8E), and a graph showing results of numerical analysis on a trabecular spacing (Tb.Sp) (see FIG. 8F), wherein the results indicate that scopolin significantly inhibits a reduction in bone density and low density in bone microstructure that are caused by menopause; and FIGS. 9A to 9C are each a graph showing levels of osteoprotegerin (OPG), which is a bone metabolism marker, in the blood of a mouse model having menopause after administering scopolin (20 mg/kg/day and 40 mg/kg/day) thereto for 12 weeks, the levels being measured in serum separated from the blood of the model mouse (see FIG. 9A) and a graph showing levels of receptor activator of nuclear factor-kappaB ligand (RANKL) in the blood of the mouse model, the levels being measured in the same manner as in measuring the levels of OPG (see FIG. 9B), and a graph showing a OPG-to-RNAKL ratios measured in the mouse model (see FIG. 9C), wherein the results indicate that scopolin significantly inhibits a decrease in the serum levels of OPG, which is a bone formation marker, and an increase in the serum levels of RANKL, which is a bone resorption marker, that are caused by menopause.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects.

The inventors of the present inventive concept have confirmed in vivo and in vitro efficacy of scopolin, which is a single compound having inhibitory effects on a reduction in bone density and low density in a bone microstructure that are caused by reduced estrogen hormones in postmenopausal women, thereby completing the present inventive concept.

According to an aspect of the present inventive concept, there is provided a pharmaceutical composition for preventing or treating postmenopausal osteoporosis in women, the pharmaceutical composition including, as an active ingredient, scopolin, a derivative thereof, or a pharmaceutically acceptable salt thereof.

In particular, the postmenopausal osteoporosis in women may be caused by a reduction in estrogen secretion, and such a reduction in estrogen secretion may induce reduction in bone density, low density in a bone microstructure, a reduction in a bone formation marker in the blood, and an increase in a bone resorption marker.

In particular, the bone formation marker may be osteoprotegerin (OPG), and the bone resorption marker may be receptor activator of nuclear factor-kappa B ligand (RANKL). However, examples of the bone formation marker and the bone resorption marker are not limited thereto.

According to an embodiment of the present inventive concept, scopolin may be represented by Formula 1 having a chemical structure of $C_{16}H_{18}O_9$:

<Formula 1>

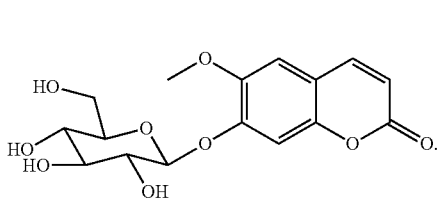

In an embodiment, the pharmaceutically acceptable salt of scopolin may be an acid addition salt which is formed by organic acid selected from the group consisting of oxalic acid, maleic acid, fumaric acid, malic acid, tartaric acid, citric acid, and benzoic acid, or by inorganic acid selected from the group consisting of hydrochloric acid, sulfuric acid, phosphoric acid, and hybrobromic acid.

When a composition disclosed herein is a pharmaceutical composition, the pharmaceutical composition may be formulated into a cream, a gel, a patch, a spray, an ointment, a plaster, a lotion, a liniment, a paste, and a cataplasma. In one or more embodiments, the pharmaceutical composition may include, in addition to scopolin, a pharmaceutically acceptable carrier. Such a pharmaceutically acceptable carrier may be any material that is commonly used in pharmaceutical preparations, and examples thereof are lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oil, but are not limited thereto. In addition, the pharmaceutical composition may include, as an additive, a lubricant, a wetting agent, a sweetener, a flavor, an emulsifier, a suspending agent, a preservative, or the like.

An administration method of the pharmaceutical composition may be determined according to the degree of postmenopausal osteoporosis in women, but local administration of the pharmaceutical composition is generally preferable. In addition, a dose of the active ingredient included in the pharmaceutical composition may vary according to an administration route, severity of a disease, and an age, a gender, and a weight of a patient, and the active ingredient may be administered once to several times per day.

According to another aspect of the present inventive concept, there is provided a health food composition for preventing or improving postmenopausal osteoporosis, the health food composition including, as an active ingredient, scopolin, a derivative thereof, or a pharmaceutically acceptable salt thereof.

The health food composition may be provided in the form of powders, granules, tablets, capsules, syrups, drinks or pills. The health food composition may be used with, in addition to scopolin which is the active ingredient, other food or food additives, and may be appropriately used according to methods used in the related art. An amount of the active ingredient to be mixed with the health food composition may be appropriately determined according to a purpose of use, such as prevention, health, or therapeutic treatment.

An effective dose of scopolin included in the health food composition may be selected within a range of the dose of the active ingredient included in the pharmaceutical composition. However, in the case of long-term intake of scopolin for the purpose of health, hygiene, or health control, the effective dose of scopolin may be within the range above. Since the active ingredient has no problem in terms of safety, the active ingredient may be used in an amount greater than the range above without difficulty.

Types of the health food are not particularly limited, and examples thereof are meat, a sausage, a bread, a chocolate, a candy, a snack, a cracker, a pizza, a ramen, other noodles, a gum, a diary product including an ice cream, various soups, a beverage, tea, a health drink, an alcoholic beverage, and a vitamin composite.

According to another aspect of the present inventive concept, there is provided a reagent composition for stimulating osteoblast differentiation, the reagent composition including, as an active ingredient, scopolin, a derivative thereof, or a pharmaceutically acceptable salt thereof.

According to another aspect of the present inventive concept, there is provided a method of stimulating osteoblast differentiation, the method including treating osteoblast with scopolin, a derivative thereof, or a pharmaceutically acceptable salt thereof.

Hereinafter, to promote understanding of one or more embodiments the present inventive concept, reference has been made to the embodiments. The present inventive concept may, however, be embodied in many different forms and should not be construed as being limited to the exemplary embodiments set forth herein. These embodiments are provided so that this disclosure will be thorough and complete, and will fully convey the concept of the present inventive concept to those skilled in the art.

<Example 1> Chemical Structure of Scopolin

A test single compound used in an animal experiment in the present inventive concept was scopolin. Scopolin has a chemical structure of $C_{16}H_{18}O_9$, and is a naturally derived single compound that is abundantly contained in Lycii radicis cortex (see FIG. 6).

<Example 2> Efficacy of Scopolin on Stimulating Osteoblasts Differentiation

Osteoblasts are derived from messenchymal stem cells, and are cells responsible for formation of new bones. Since the role of osteoblasts is important after menopause where female estrogens are rapidly reduced, efficacy of scopolin on proliferation and differentiation of osteoblasts was examined.

Cytotoxicity of scopolin was evaluated by cell proliferation analysis using an EZ-Cytox Enhanced Cell Viability Assay Kit using a water-soluble tetrazolium salt. In detail, MC3T3-E1 cells ($3 \times 10^3$ cells/well), which are osteoblasts, were cultured in an alpha-minimum essential medium (α-MEM) supplemented with 10% bovine fetus serum, 1 mM sodium pyruvate, 100 unit/L penicillin, and 100 mg/L streptomycin at a temperature of 37° C. under conditions provided with 5% $CO_2$, and then, the cells were treated with scopolin at three different concentrations (1 μg/ml, 5 μg/ml, and 10 μg/ml) and cultured for 2 days. Next, the tetrazolium salt was applied to each of the cultured cells and a sample, followed by being cultured at a temperature of 37° C. for 2 hours, and then, absorbance thereof was measured at a wavelength of 450 nm. In comparison with a control group treated with physiological saline, it was confirmed that scopolin had no adverse effect on the proliferation of the MC3T3-E1 cells in all of the experimental groups that were treated with scopolin at concentrations of 1 μg/ml (Sco1), 5 μg/ml (Sco5), and 10 μg/ml (Sco10) (see FIG. 7A).

The efficacy of scopolin on the differentiation of osteoblasts was evaluated by using the MC3T3-E1 cells. Ascorbic acid (50 μg/ml) and β-glycerophosphate (10 mM), which are osteoblast inducers, were added to the MC3T3-E1 cells, to thereby induce the differentiation for 3 days. Then, the resulting cells were treated with scopolin. Scopolin was dissolved in 1% dimethyl sulfoxide (DMSO) aqueous solution, and then, was applied to the MC3T3-E1 cells at concentrations of 1 μg/ml (Sco1), 5 μg/ml (Sco5), and 10 μg/ml (Sco10). The resulting cells were cultured for additional 48 hours. As a control group, cells were cultured in the same amount of 1% DMSO aqueous solution in which scopolin was not treated. To determine the efficacy of scopolin on the differentiation of osteoblasts, the activity of alkaline phosphatase (ALP) was measured. In detail, the cells that were washed using physiological saline and dissolved using a lytic agent was treated with p-nitrophenyl phosphate, which is a substrate of ALP, and then, cultured at a temperature of 37° C. for 1 hour. Subsequently, 0.5N NaOH, which is a reaction terminating solution, was added the cultured cells, and then, absorbance thereof was measured at a wavelength of 405 nm. As a result, it was confirmed that the differentiation of osteoblasts statistically significantly increased in the experimental groups treated with scopolin at a concentration of 5 μg/ml (Sco5) or 10 μg/ml (Sco10) (see FIG. 7B)(*: $p<0.05$ vs. negative control group). In addition, as a result of evaluating the differentiation of osteoblasts through ALP staining, it was confirmed that the cells treated with 5 μg/ml of scopolin showed increased ALP staining (see FIG. 7C).

The mineralization of osteoblasts was analyzed by an Alizarlin red S staining method after experimental groups and a control group were each treated with 5 μg/ml of scopolin and cultured. As a result, it was confirmed that the cells treated with scopolin showed increased minieralization (see FIG. 7D). That is, it was confirmed that scopolin was effective in stimulating the differentiation of osteoblasts.

<Example 3> Efficacy of Scopolin on Inhibiting Postmenopausal Osteoporosis in Ovariectomized Menopausal Mouse Model To evaluate in vivo efficacy of scopolin, a 10-week-old ddY female ovariectomized (OVX)-mouse was used a menopausal animal model (ovariectomy was performed on the 8-week-old mouse, and the mouse was additionally raised for 2 weeks). Regarding control groups, a Shame mouse that was subjected to laparotomy, but was not subjected to ovariectomy, (normal control group), and an OVX mouse to which physiological saline was added (negative control group) were used, and in addition, a strontium chloride ($SrCl_2$) mouse in which 20 mg/kg/day of $SrCl_2$, which is a compound having an effect in enhancing bone mineral density, was administered by oral injection to an OVX mouse was used as a positive control group in the test for bone mineral density improvement efficacy. Here, an experimental group was prepared by administering scopolin at a dose of 20 mg/kg/day and 40 mg/kg/day by oral injection. The 10-week-old sham-operated mouse and the ddY OVX-mouse were purchased at Central Lab. Animal Inc., and then, were moved to a clean animal breeding room after spending 1 week of purification period in the laboratory animal quarantine room. These mice were individually weighed to be classified into experimental groups without a statistically significant difference in weight. Scopolin used in the experiment was dissolved in 1% DMSO aqueous solution to be prepared as a test solution. In order to bring these mice in the laboratory animal center, a radiation irradiation company, SOYAGREENTEC Inc., was commissioned for sterilization operations using gamma irradiation.

At the beginning of the animal experiment, a PIXImus bone densitometer was used to measure initial bone mineral density (BMD) of the mice. The mice were anesthetized by injecting 50 μl of a mixed anesthetic of zoletil and rompun (a mixture of zoletil and rompun at a ratio of 1:2 was diluted with physiological saline at a ratio of 2:3), and then, were fixed to a bone mineral density measuring frame to measure bone mineral density. After 6 weeks and 12 weeks of the injection of scopolin to the mice, the bone mineral density of the mice was measured by using the PIXImus bone densitometer. After the completion of the experiment during 12 weeks, blood sampling and removal of femoral bone were performed, and micro-CT was taken thereon. In the micro-CT images, bone volume ratios (BV ratios, %), trabecular thickness (Tb.Th), trabecular number (Tb.N), and trabecular spacing (Tb.Sp) were numeralized and analyzed.

In comparison with the normal Shame mouse that was not subjected to ovariectomy, the OVX mouse that was subjected to ovariectomy showed significantly reduced bone mineral density after 6 weeks and 12 weeks of scopolin treatment (see FIG. 8A), and micro-CT images thereof showed significantly low bone density of the bone structure of the mice (see FIG. 8B). In addition, the analysis results showed significantly low BV ratios (see FIG. 8C), small Tb.Th (see FIG. 8D), small Tb.N (see FIG. 8E), and high Tb.Sp (see FIG. 8F). However, in the experimental groups to which scopolin was administered at a dose of 20 mg/kg/day and 40 mg/kg/day for 12 weeks, it was confirmed that the decrease in the bone mineral density and low density of the bone structure that were caused by the menopause were inhibited (see FIGS. 8A and 8B), and that the reduction in BV ratios, Tb. Th, and Tb. N and the increase in Tb. Sp were inhibited (see FIGS. 8C, 8D, 8E, and 8F). Such results were similar with those obtained by the $SrCl_2$ mouse which is the positive control group. In addition, in the statistical analysis, the significance of the efficacy of scopolin was also confirmed (*: $p<0.05$ vs. OVX negative control group).

Next, the changes of blood metabolism markers in the blood were examined. After 12 weeks of the experiment performed on the postmenopausal mouse model, the blood sampling was performed thereon, and serum samples were collected therefrom. The serum protein levels of osteoprotegerin (OPG), which is a bone formation marker, and receptor activator of nuclear factor-kappa B ligand (RANKL), which is a bone resorption marker, were analyzed by ELISA. In comparison with the normal Shame mouse that was not subjected to ovariectomy, the OVX mouse that was subjected to ovariectomy showed significantly decreased levels of OPG (see FIG. 9A), increased levels of RANKL (see FIG. 9B), and decreased OPG/RANKL ratios (see FIG. 9C). However, in the experimental groups to which scopolin was administered at a dose of 20 mg/kg/day and 40 mg/kg/day for 12 weeks, it was confirmed that the decrease in the level of OPG, which is the bone formation marker in the blood, the increase in the level of RANKL, which is the bone resorption marker, and the decrease in the OPG/RANKL ratios were inhibited (see FIGS. 9A, 9B, and 9C). Such results were similar with those obtained by the $SrCl_2$ mouse which is the positive control group. In addition, in the statistical analysis, the significance of the efficacy of scopolin was also confirmed (*: $p<0.05$ vs. OVX negative control group).

As described above, the present inventive concept provides a pharmaceutical composition for preventing or treating postmenopausal osteoporosis in women, the pharmaceutical composition including, as an active ingredient, scopolin, a derivative thereof, or a pharmaceutically acceptable salt thereof, wherein scopolin has efficacy on stimulating osteoblast differentiation and is effective in inhibiting reduction of bone mineral density after menopause, low density of a bone microstructure, a decrease in a bone formation marker in the blood, and an increase in a bone resorption marker. Therefore, scopolin and a composition including the same as an active ingredient are expected to be used as a pharmaceutical agent for the prevention, improvement, and treatment of postmenopausal osteoporosis in women.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims.

What is claimed is:

1. An in vitro method of stimulating osteoblast differentiation, the method comprising treating osteoblast with scopolin, or a pharmaceutically acceptable salt thereof, wherein the osteoblast differentiation is stimulated.

* * * * *